United States Patent
Sopchik et al.

(10) Patent No.: US 9,517,999 B2
(45) Date of Patent: Dec. 13, 2016

(54) PROCESS FOR PURIFYING (METH)ACRYLIC ACID

(71) Applicant: Rohm and Haas Company, Philadelphia, PA (US)

(72) Inventors: Alan E. Sopchik, Deer Park, TX (US); Stephen T. Cohn, Spring, TX (US)

(73) Assignee: Rohm and Haas Company, Philadelphia, PA (US)

( * ) Notice: Subject to any disclaimer, the term of this patent is extended or adjusted under 35 U.S.C. 154(b) by 0 days.

(21) Appl. No.: 14/766,541

(22) PCT Filed: Mar. 7, 2014

(86) PCT No.: PCT/US2014/021657
§ 371 (c)(1),
(2) Date: Aug. 7, 2015

(87) PCT Pub. No.: WO2014/149967
PCT Pub. Date: Sep. 25, 2014

(65) Prior Publication Data
US 2015/0368177 A1 Dec. 24, 2015

Related U.S. Application Data

(60) Provisional application No. 61/789,395, filed on Mar. 15, 2013.

(51) Int. Cl.
C07C 51/487 (2006.01)

(52) U.S. Cl.
CPC .................. C07C 51/487 (2013.01)

(58) Field of Classification Search
CPC .................................................. C07C 51/487
See application file for complete search history.

(56) References Cited

U.S. PATENT DOCUMENTS

| | | |
|---|---|---|
| 3,725,208 A | 4/1973 | Maezawa et al. |
| 3,893,895 A | 7/1975 | Dehnert et al. |
| 4,625,059 A | 11/1986 | Shibano et al. |
| 4,828,652 A | 5/1989 | Schropp |
| 5,208,370 A | 5/1993 | Bauer, Jr. et al. |
| 5,552,175 A | 9/1996 | Camburn |
| 5,571,386 A | 11/1996 | Bauer, Jr. et al. |
| 5,746,892 A | 5/1998 | Bauer, Jr. et al. |
| 5,759,358 A | 6/1998 | Bauer, Jr. et al. |
| 5,760,283 A | 6/1998 | Roof et al. |
| 6,753,383 B2 | 6/2004 | Schaefer et al. |
| 8,242,308 B2 | 8/2012 | Ho et al. |

FOREIGN PATENT DOCUMENTS

| | | | |
|---|---|---|---|
| EP | 169254 | | 1/1986 |
| FR | 2171910 | | 2/1972 |
| GB | 1346737 | | 2/1974 |
| JP | 50000014 | | 1/1975 |
| JP | 57088143 | | 6/1982 |
| JP | 2012-120708 | * | 6/2012 |

OTHER PUBLICATIONS

V. Bednarik et al., Removal of formaldehyde from acrylic acid production wastewater:, Environmental Engineering Science, vol. 20, No. 6, Jan. 1, 2003, p. 703-707.
Kallen, "The mechanism of reactions involving Schiff base intermediates. Thiazolidine formation from L-cysteine and formaldehyde", Journal of the American Chemical Society, Nov. 17, 1971, pp. 6236-6248.
Padwa, "A Dipolar Cycloaddition Approach to Pyrrolo[1,2-a]indoles Using N-[(Trimethylsilyl)methyl]-Substituted Indoles", J. Org. Chem., 1989, 54, pp. 644-653.

* cited by examiner

*Primary Examiner* — Shailendra Kumar
(74) *Attorney, Agent, or Firm* — Edward L. Brant

(57) ABSTRACT

A process for producing a grade of (meth)acrylic acid having residual formaldehyde levels of under 100 parts per million.

11 Claims, No Drawings

US 9,517,999 B2

PROCESS FOR PURIFYING (METH)ACRYLIC ACID

CROSS-REFERENCE TO RELATED APPLICATIONS

This application is a 371 of PCT/US14/21657, filed on Mar. 7, 2014, and claims priority from provisional application Ser. No. 61/789,395, filed Mar. 15, 2013, which is incorporated herein by reference in its entirety.

BACKGROUND OF THE INVENTION

The invention relates to a process for purifying (meth) acrylic acid. More specifically, the process is a process that provides (meth)acrylic acid containing very low levels of residual aldehyde.

In the manufacture of acrylic acid by the catalytic oxidation of propylene, acrylic acid ("AA") and oxidation by-products initially are obtained by absorbing or quenching reactor effluent gases with water to produce an aqueous AA solution before further purification. Fouling, e.g., the in situ formation of acrylic polymer on the processing equipment internals, is a major problem associated with the production of AA. Fouling can be exacerbated by impurities in the AA solution.

Aldehydes are an undesirable impurity, as they can cause fouling in the manufacturing process, and as they cause problems when present in polymer grade AA. The presence of these aldehyde impurities and their hydrates in aqueous media is detrimental to downstream acrylic acid processing for multiple reasons including: (1) the demonstrated ability of these contaminants to destabilize AA by initiating acrylic acid free radical polymerizations, (2) active participation in downstream process column fouling by self polymerization, co-polymerization with other reactive monomers, and reaction in some instances with process inhibitors, and (3) negatively impacting product quality by contamination of the final acrylic acid product if not fully removed beforehand. The conversion of these reactive aldehyde impurities to non-reactive heavies should ideally be performed as early in the acrylic acid purification process as possible.

In currently commercial AA processes, it is common to find a crystallizer and/or several distillation columns, or towers. However, as taught in U.S. Pat. No. 8,242,308, each tower requires the addition of fresh polymerization inhibitor to inhibit polymer fouling.

Furthermore, conventional fractional distillation alone is not effective in reducing aldehyde impurities to necessary levels to produce pure grade acrylic acid ("PGAA"), which is useful for the application of purposely producing polymers. To obtain PGAA, less pure AA from either the extraction/distillation or direct distillation procedure must be purified beyond that achieved by conventional fractional distillation because residual impurities, particularly the aldehydes, interfere with PGAA-related end use polymerization reactions. For these applications, aldehyde levels individually must be below about ten parts per million (ppm), more preferably below five ppm, and most preferably below one ppm. PGAA having these aldehyde levels is useful in producing, for example, superabsorbent polymers and polymers efficient as dispersants for oil well drilling muds and as flocculating agents.

One known method of producing PGAA applies aldehyde scavengers to dry AA in order to reduce aldehyde levels. Specifically, U.S. Pat. No. 5,759,358 produces PGAA by sequentially applying, during the final stages of distillation, selected groups of amines to reduce acrolein and furfural.

It would be desirable to be able to reduce aldehyde content early in the manufacturing process. Benefits of early aldehyde removal include, but are not limited to, reduced costs associated with fouling-related column shut-down/clean-out and associated lost AA production.

SUMMARY OF THE INVENTION

The invention is such a process for producing a pure grade (meth)(meth)acrylic acid, the process comprising contacting an aqueous crude (meth)acrylic acid, which comprises formaldehyde as an impurity, with at least 0.5 molar equivalent of cysteine per mole of formaldehyde impurity, wherein the contacting is conducted under conditions sufficient to reduce the concentration of the formformaldehyde impurity to less than 100 ppm per 100 weight parts (meth)acrylic acid.

Surprisingly, the reaction of cysteine with aldehydes proceeds efficiently in the presence of aqueous organic acids such as acetic and (meth)acrylic acids.

DETAILED DESCRIPTION OF THE INVENTION

As used herein, "a," "an," "the," "at least one," and "one or more" are used interchangeably. The terms "comprises," "includes," and variations thereof do not have a limiting meaning where these terms appear in the description and claims. Thus, for example, an aqueous composition that includes particles of "a" hydrophobic polymer can be interpreted to mean that the composition includes particles of "one or more" hydrophobic polymers.

Also herein, the recitations of numerical ranges by endpoints include all numbers subsumed in that range (e.g., 1 to 5 includes 1, 1.5, 2, 2.75, 3, 3.80, 4, 5, etc.). For the purposes of the invention, it is to be understood, consistent with what one of ordinary skill in the art would understand, that a numerical range is intended to include and support all possible subranges that are included in that range. For example, the range from 1 to 100 is intended to convey from 1.01 to 100, from 1 to 99.99, from 1.01 to 99.99, from 40 to 60, from 1 to 55, etc.

Also herein, the recitations of numerical ranges and/or numerical values, including such recitations in the claims, can be read to include the term "about." In such instances the term "about" refers to numerical ranges and/or numerical values that are substantially the same as those recited herein.

As used herein, the use of the term "(meth)" followed by another term such as acrylate refers to both acrylates and methacrylates. For example, the term "(meth)acrylate" refers to either acrylate or methacrylate; the term "(meth) acrylic" refers to either acrylic or methacrylic; and the term "(meth)acrylic acid" refers to either acrylic acid or methacrylic acid.

Unless stated to the contrary, or implicit from the context, all parts and percentages are based on weight and all test methods are current as of the filing date of this application. For purposes of United States patent practice, the contents of any referenced patent, patent application or publication are incorporated by reference in their entirety (or its equivalent U.S. version is so incorporated by reference) especially with respect to the disclosure of definitions (to the extent not inconsistent with any definitions specifically provided in this disclosure) and general knowledge in the art.

In the context of this invention, the terms "crude (meth) acrylic acid" (CAA), "aqueous crude (meth)acrylic acid"

and "aqueous (meth)acrylic acid" are interchangeable and are used to describe (meth)acrylic acid that contains by-product contaminants, which are produced during the production of (meth)acrylic acid, and that has a water content of 5% to 80% or more by weight. Total contaminant levels can comprise up to 6-7 wt. % but typically are present at less than 5%. These contaminants can include aliphatic and aromatic aldehydes, e.g., acetaldehyde, propionaldehyde, and benzaldehyde; heteroatom containing aldehydes, e.g., furfural and 3-hydroxy propionaldehyde; unsaturated aldehydes, e.g., acrolein and crotonaldehyde, organic acids such as maleic, acetic, formic, and 3-hydroxy propionic acid, as well as non-aldehyde or acid type contaminants such as ketones, esters, protoanemon (PTA) or its dimer.

The process of this disclosure comprises contacting cysteine with aqueous (meth)acrylic acid that comprises aldehyde impurities and that optionally comprises acetic acid.

The process of the invention employs 2-amino-3-mercaptopropionic acid, which is also called cysteine. It exists in various forms, including the D isomer, the L isomer, and racemic mixtures. For the purposes of the invention, any form of cysteine can be employed, including any combination thereof. Advantageously, the amount of cysteine employed is an amount that is sufficient to reduce the concentration of the formaldehyde impurity to less than 100 ppm per 100 weight parts (meth)acrylic acid. In various embodiments of the invention, the cysteine is employed in an amount sufficient to reduce the concentration of the formaldehyde impurity to less than 50 ppm per 100 weight parts (meth)acrylic acid, or less than 25 ppm, or less than 10 ppm. The amount of the cysteine to be employed can be determined by measuring the concentration of the impurities in the CAA to be treated. In various embodiments of the invention, the amount of cysteine employed per mole of formaldehyde impurity is at least 0.5 molar equivalent, or at least one molar equivalent. In various embodiments of the invention, the amount of cysteine employed per mole of formaldehyde impurity is at most 10 molar equivalents, is at most 5 molar equivalents, or is at most 2 molar equivalents. As a practical matter, the amount of cysteine employed may be at or near the minimum amount necessary to achieve the desired level of purification.

The process of making (meth)acrylic acid is well known to those skilled in the art. For example, acrylic acid is commonly produced by the catalytic gas phase oxidation of propane and/or propylene. The gas phase commonly is contacted with water to condense the gas. This contacting is commonly conducted in an absorber or quench tower. It can also be conducted in a dehydration tower as taught in U.S. Pat. No. 8,242,308. The resulting wet AA liquid can be employed as the aqueous CAA for the process of this invention.

Aldehydes typically exist in CAA process streams. These aldehyde impurities are formed during the oxidation step of acrylic acid production. Aldehydes are well known compounds of the formula RC(O)H, wherein R is H, or a moiety comprising aliphatic and/or aromatic character. Examples of aldehydes include formaldehyde, acrolein, furfural, benzaldehyde and acetaldehyde. The aqueous CAA contains aldehyde impurities at a total concentration of from 0.001 to 1.5 weight parts per 100 weight parts acrylic acid. Individual aldehyde impurity content before treatment can vary anywhere from around 1 wt % down to less than 100 ppm, depending on the aldehyde.

The generalized reaction between 2-amino-3-mercaptopropionic acid (isomer unspecified) and an aldehyde, is given below.

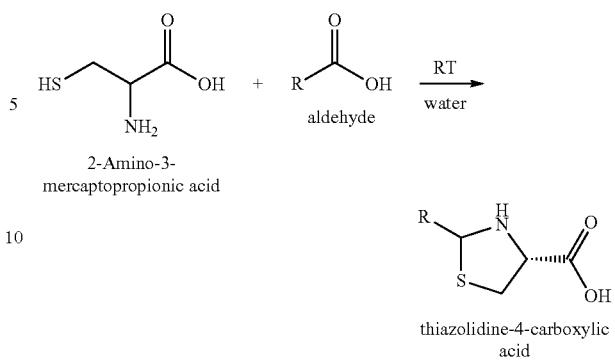

2-Amino-3-mercaptopropionic acid aldehyde thiazolidine-4-carboxylic acid

The cysteine advantageously is employed as a solution in a suitable solvent, such as water or CAA. While a wide variety of solvents are suitable, in practice it is preferred to use water or CAA, as doing so does not introduce additional materials to the system.

The cysteine can be contacted with the aqueous CAA in any suitable manner. The cysteine can be added, preferably as a solution in water, to the absorber column where the (meth)acrylic acid vapor from the reactor is absorbed or mixed with water. In one embodiment, an aqueous cysteine solution is added along with process water being added to the absorber to absorb the (meth)acrylic acid vapor. In another embodiment, the cysteine is added along with solutions of free radical polymerization inhibitors such as, for example, hydroquinone, 4-hydroxy TEMPO, manganese acetate, and other inhibitors that are well known in the art, and combinations thereof. It is possible to add the cysteine in more than one stream and/or in more than one location. Cysteine can be, for example, either co-injected in separate streams or as a single pre-mixed solution of inhibitor and cysteine.

The CAA that has been contacted with cysteine may be further treated according to purification methods well known to those skilled in the art, e.g., distillation and/or crystallization.

An advantage of the process of the invention is that formaldehyde, acrolein and other reactive aldehydes are removed early in the AA purification process, with the added benefit of reducing the tendency for the AA to polymerize while being purified. Thus, cysteine can be used effectively in partially purifying (meth)acrylic acid in a continuous process step prior to feeding to the final fractional distillation column or crystallization unit yielding PGAA and avoiding some of the tendency of (meth)acrylic acid to polymerize while being purified.

The contacting may be conducted under any conditions that are consistent with the conditions of the related AA manufacturing process. In one embodiment of the invention, the temperature of the gas stream entering the contacting apparatus, e.g., an absorber etc., can range from 170 to 350° C. In various embodiments of the invention, the average temperature in the contacting apparatus is from 25 to 100° C., or from 60 to 70° C., or from 70 to 80° C.

The process of the invention can be operated as a batch or, preferably, as a continuous process. In one embodiment of the invention, fouling advantageously is reduced compared to current commercial processes.

Specific Embodiments of the Invention

The following examples are given to illustrate the invention and should not be construed as limiting its scope.

EXAMPLES

In aqueous organic acids, using several different aldehydes and at temperatures of up to 85° C., thiazolidines are formed in high yields. An example, namely, reacting 2-amino-3-mercaptopropionic acid (cysteine) with formaldehyde/formalin is shown as follows:

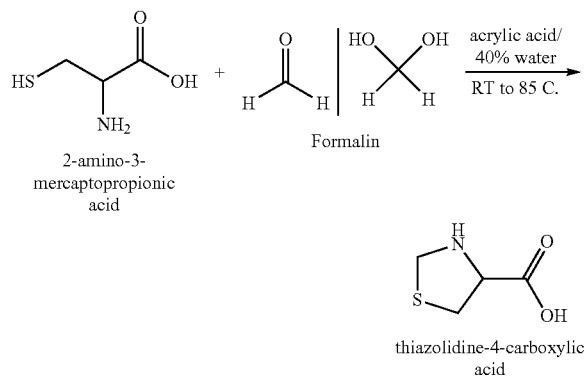

Example 1

Starting with a 30% aqueous acrylic acid solution containing 0.39 wt % formaldehyde (as formalin), slightly greater than one molar equivalent of 2-amino-3-mercaptopropionic acid is added then heated in an 85° C. oil bath for 15 min. The reaction produces thiazolidine-4-carboxylic acid as the product. Chemical shifts of the solid by proton NMR match literature values. The amount of formaldehyde "removed" from solution is calculated to be 82.9 mol % (quantified by proton NMR) based on the isolated yield of thiazolidine-4-carboxylic acid. The results are summarized in Table 1.

TABLE 1

Product distribution from the reaction of 2-amino-3-mercaptopropionic acid) and formaldehyde (formalin) at 85° C. in 30% aqueous acrylic acid.

|  | 2-amino-3-mercaptopropionic acid | Formaldehyde | Thiazolidine-4-carboxylic acid |
| --- | --- | --- | --- |
| starting mmols | 0.619 | 0.644 | 0.000 |
| after 15 min-@ 85° C. (mmol) | 0.085 | 0.110 | 0.542 |
| % reduction of Formaldehyde (%) |  | 82.9 |  |

Example 2

The effectiveness of the reaction of 2-amino-3-mercaptopropionic acid with aldehydes is further studied using a sample of acrylic acid absorber effluent containing about 40 wt. % water and the aldehyde impurities shown in Table 3. By proton NMR, a significant portion of the formaldehyde content is found to be present as the hydrate. Using the procedure of Example 1, except as noted, 2-amino-3-mercaptopropionic acid is added at concentrations of 0.5, 1.2, and 2.0 molar equivalents relative to the formaldehyde content. The solution is then heated in a 85° C. oil bath for one hour and analyzed by proton NMR. At all concentrations of 2-amino-3-mercaptopropionic acid, acrolein content is reduced to non-detectable levels (proton NMR) whereas formaldehyde requires a 1:1 molar ratio with 2-amino-3-mercaptopropionic acid before a large drop in concentration is noted. A 26% reduction of furfural is obtained with 2.0 equivalents 2-amino-3-mercaptopropionic acid, in the presence of the other aldehydes. The results are summarized in Table 2.

TABLE 2

Product distribution from the reaction of 2-amino-3-mercaptopropionic with selected process aldehyde contaminants contained in acid aqueous AA absorber effluent. Reaction at 85° C.

| Molar eq. 2-amino-3-mercaptopropionic acid based on formaldehyde | Formaldehyde (ppm) | Acrolein (ppm) | Furfural (ppm) |
| --- | --- | --- | --- |
| 0 | 6496 | 127 | 127 |
| 0.5 | 2606 | 0 | 123 |
| 1.2 | 31 | 0 | 131 |
| 2 | 31 | 0 | 94 |

In summary, 2-amino-3-mercaptopropionic acid shows unexpectedly high selectivity in aqueous acrylic acid in its ability to scavenge formaldehyde (~1:1 molar ratio). In the process of doing so, acrolein, which is present at lower levels, is completely eliminated. Removing both of these impurities, especially when done early in the manufacturing process, can significantly reduce fouling due to unwanted polymerization in acrylic acid separation and refining sections, thus leading to significant savings in operations, e.g., reduced shut down and clean out, and reduced raw material, e.g., inhibitors, costs.

What is claimed is:

1. A process for producing a pure grade (meth)acrylic acid, comprising contacting an aqueous crude (meth)acrylic acid, which comprises formaldehyde as an impurity, with at least 0.5 molar equivalent of cysteine per mole of formaldehyde impurity, wherein the contacting is conducted under conditions sufficient to reduce the concentration of the formaldehyde impurity to less than 100 ppm per 100 weight parts (meth)acrylic acid, wherein the aqueous crude (meth)acrylic acid comprises at least 5 wt. % water, and wherein the contacting is conducted in an absorber, quench tower, or dehydration column.

2. The process of claim 1 wherein the amount of cysteine is at least 1 molar equivalent.

3. The process of claim 1 wherein the amount of cysteine is from 1 to 10 molar equivalents.

4. The process of claim 1 wherein the amount of cysteine is from 1 to 5 molar equivalents.

5. The process of claim 1 wherein the amount of cysteine is from 1 to 2 molar equivalents.

6. The process of claim 1 wherein the aqueous crude (meth)acrylic acid comprises from 5 to 80 wt. % water.

7. The process of claim 1 wherein the concentration of the formaldehyde impurity is reduced to less than 50 ppm per 100 weight parts (meth)acrylic acid.

8. The process of claim 1 wherein the concentration of the formaldehyde impurity is reduced to less than 25 ppm per 100 weight parts (meth)acrylic acid.

9. The process of claim 1 wherein the concentration of the formaldehyde impurity is reduced to less than 10 ppm per 100 weight parts (meth)acrylic acid.

10. The process of claim 1 wherein the process is continuous.

11. The process of claim 1 wherein the crude acid further comprises acrolein prior to the contacting with cysteine.

* * * * *